United States Patent [19]

McDaniel et al.

[11] 4,209,316
[45] Jun. 24, 1980

[54] METHOD AND MATERIALS FOR ENHANCEMENT OF PLANT GROWTH CHARACTERISTICS

[75] Inventors: Robert G. McDaniel; B. Brooks Taylor, both of Tucson, Ariz.

[73] Assignee: University Patents, Inc., Norwalk, Conn.

[21] Appl. No.: 912,061

[22] Filed: Jun. 2, 1978

[51] Int. Cl.$^2$ .................... A01N 21/02; A01N 13/00; A01N 9/36; A01N 9/22
[52] U.S. Cl. .......................................... 71/77; 71/80; 71/82; 71/86; 71/92
[58] Field of Search .......................... 71/77, 82, 86, 92

[56] References Cited

U.S. PATENT DOCUMENTS

| | | | |
|---|---|---|---|
| 2,314,091 | 3/1943 | Jones | 71/77 |
| 2,396,468 | 3/1946 | Ladd | 71/77 |
| 2,653,087 | 9/1953 | Skoog | 71/82 |
| 2,921,410 | 1/1960 | Merritt | 71/77 |
| 3,100,149 | 8/1963 | Ruge | 71/77 |
| 3,172,816 | 3/1965 | Swintosky | 71/DIG. 1 |
| 3,413,111 | 11/1968 | Braunholtz et al. | 71/82 |
| 4,050,919 | 9/1977 | Motomura et al. | 71/86 |

FOREIGN PATENT DOCUMENTS

| | | | |
|---|---|---|---|
| 614171 | 2/1961 | Canada | 71/82 |

OTHER PUBLICATIONS

Ghosh et al., "Inhibition of Seedling Growth, etc.;" (1977), CA86, No. 151414q. (1977).
Hartung, "Importance of C-AMP etc.;" (1973), CA79 No. 14323a, (1973).
Kobayashi et al., "Growth Promoting Agents, etc.;" (1973), CA80, No. 44694k, (1974).
Kamisaka et al., "Effects of Cyclic AMP and Gibberellic etc.," (1972), Plant & Cell Physiol. 13, pp. 167–173 (1972).
Shannon et al., "Influence of Seed Pretreatments etc.;" (1976), Agron. J. 69, pp. 619–622 (1977).
Barendse et al., "Evidence Against the Involvement, etc.;" (1975), Plant Science Letters 4, pp. 217–213 (1975).
Stinson et al., "An Evaluation of the Effects of Five Buffers, etc.;" (1967), Can. J. Biochem. 46, pp. 43–50, (1968).

*Primary Examiner*—Glennen H. Hollrah
*Attorney, Agent, or Firm*—Merriam, Marshall & Bicknell

[57] ABSTRACT

Plant seed and seedlings are treated with compositions including nucleosides and/or nucleotides and with a buffering agent to achieve enhancement of emergence and seedling growth characteristics. In a preferred embodiment, seed is surface treated with an aqueous solution of $2 \times 10^{-2}$ M adenosine monophosphate buffered at about pH 7.0 with phosphoric acid salts.

10 Claims, No Drawings

METHOD AND MATERIALS FOR ENHANCEMENT OF PLANT GROWTH CHARACTERISTICS

BACKGROUND OF THE INVENTION

The present invention relates generally to enhancement of growth characteristics of plants and more particularly to improvements in methods and materials for treating seed and seedlings with nucleosides and nucleotides to effect enhancement of emergence and seedling vigor characteristics.

The prior art is rich in proposals of methods and materials for seed, seedling, and mature plant treatment to enhance growth characteristics and resistance of plant tissue to plant pathogens. The materials commonly applied to seed and growing plants range from simple substances such as water (as a pre-planting, hydration treatment for seed), to inorganic salt solutions, to complex growth regulators, antibiotics and the like.

Basic research in plant physiology has included numerous studes of plant cell respiration. Of particular interest to the background of the invention have been studies directed to the role of nucleosides, nucleotides and inorganic phosphate in mitochondrial function, e.g., Holm et al., *Weed Science* 20: 209-212 (1972); Santarius et al. *Biochemica et Biophysica Acta* 102: 39-54 (1965); and Hanssens et al., *J. Bacteriology* 125: 829-836 (1976). These studies are correlated to investigations, by the inventor and others, directed to the agronomic use of purines, pyrimidines, nucleosides and nucleotides as seed treating agents, e.g., Cole et al. *Crop Science*, 14, 451-454 (1974); and Jung et al., *Plant Physiology*, 171, 583-584 (1967).

In early 1974, the applicants and their co-workers discovered that the application of nucleosides and nucleotides to seed prior to planting provided salutory effects on overall germination percentages (seedling emergence) and various other indicators of seedling vigor in plants grown from the treated seed. It was found that seeds treated with, for example, adenosine monophosphate (AMP) and cyclic adenosine monophosphate (c-AMP) showed substantial increases in seedling emergence and vigor. The most profound effects were noted in those plants which are extremely sensitive to "environmental stresses", i.e., low temperature and/or high salt and/or soil and airborne pathogens during germination. While the precise mechanism of action of the treatment has not been fully elucidated, it is believed that small quantities of nucleosides and nucleotides are transported through the seed coat and enhance the respiratory efficiency of mitochondria—thus allowing the germinating plant to make more effective use of stored fuel supplies in the seed.

It was unfortunately the case that the emergence and seedling growth characteristics observed for AMP and c-AMP treated seed in laboratory tests were simply not reproducable in field experiments; and, while some degree of improvement was observed as a result of treatment, it was inconsistent and did not appear to justify the treatment materials and processing costs. The reasons for the essential failure of seed treatment to produce the desired effects under field conditions were not known. Prior to the present invention, then, the art had progressed to the stage at which the potential for enhancement of growth characteristics by treatment of seed with nucleotides such as AMP was noted, but no effective means was available to ensure the achievement of such effects under normal growth conditions.

BRIEF SUMMARY

Growth characteristics of plant seed and seedlings are enhanced by treatment with nucleosides and/or nucleotides together with a non-phytotoxic buffering agent. The use of buffering agents according to the invention not only increases the effectiveness of the nucleoside or nucleotide but also assures the retention of effectiveness under field conditions.

Nucleosides and nucleotides useful in the practice of the invention include purine ribosides, such as adenosine and guanosine, as well as their mono-, di and triphosphate esters. Adenosine monophosphate (AMP) and cyclic adenosine monophosphate are preferred on the basis of effectiveness, cost and availability.

In the practice of the invention, buffering agents —substances or combinations of substances which in solution impart resistance to pH change upon addition of an acid or base—are generally selected on the basis of their potential phytotoxicity and their general buffering "capacity" within selected pH ranges consistent with such factors as solubility of the nucleoside and nucleotide, soil conditions, prior seed treatment and the like. Within the framework of these criteria, phytotoxic substances are ordinarily to be avoided as buffering agent components, while phosphate, tris(hydroxymethyl)aminomethane and similar buffering agent component materials which possess good buffering capacity in moderately acidic to basic solutions are preferred.

Treatment with the nucleoside or nucleotide may be effected in a step separate from treatment with the buffering agent although concurrent treatment, e.g., with aqueous solutions of both materials, is preferred. Application of the materials to seeds may be made before planting by means of a liquid bath or spray and after planting by means of layby application to the seed bed. Emerging seedlings may be foilar sprayed or dipped. The application method of choice involves incorporation of aqueous treating solutions within existing schemes for commercials processing of seed. Cotton seed, for example, may be treated according to the invention following the acid de-linting of seed and such treatment may be effected simultaneously with application of fungicides and the like.

Also provided by the invention are novel reagent compositions of matter including dry and aqueous mixtures of nucleoside and/or nucleotide and buffering agent which are especially suitable for use as treating agent for plant seed and seedlings to enhance growth characteristics.

Numerous other aspects and advantages of the invention will become apparent to those skilled in the art upon consideration of the following detailed description and illustrative examples.

DETAILED DESCRIPTION

According to the invention, the effectiveness of the treatment of plant seed and seedlings with nucleotides and/or nucleosides is markedly enhanced by sequential or concurrent treatment with a non-phytotoxic buffering agent. Contemplated by the invention are novel compositons of matter comprising mixtures of one or more selected nucleosides and nucleotides and a buffering agent in either dry or, preferably, aqueous form, as well as the use of the compositions as treating materials for plant seed and seedlings.

The nucleosides and nucleotides useful in the practice of the invention include purine ribosides such as adenosine and guanosine as well as their phosphate esters, e.g., adenosine monophosphate, adenosine diphosphate and adenosine triphosphate. Practical considerations of cost, stability and widespread commercial availability render adenosine monophosphate (AMP) and cyclic adenosine monophosphate (c-AMP) preferable for large scale agronomic purposes. Within this context, AMP in its free acid (monohydrate) form is as stable and somewhat less expensive than the corresponding sodium salt form of AMP. Sodium salts of adenosine diphosphate and adenosine triphosphate are ordinarily less expensive and more stable than the free acid form, but still less stable than AMP.

Buffering agents suitable for use in the invention are numerous and the selection of a particular combination of a weak acid and its salt, or weak base and its salt, or amphoteric substance is largely a matter of choice—subject only to the practical consideration that the agent exhibit appropriate buffering properties and be essentially non-phytotoxic. Expectedly, the use of phytotoxic materials, would likely result in deleterious effects outweighing plant growth enhancement attending nucleoside or nucleotide treatment. Buffering agents commonly held to display biotoxic properties include: borate buffers, barium salt buffers, cacodylic acid buffers, lithium salt buffers, hydrocyanic acid buffers, benzoic acid salt buffers, and oxalic acid salt buffers. Buffering agents which are relatively non-toxic and hence suitable for use in practice of the invention include: phosphate buffers (including ammonium, potassium, sodium and calcium salts), buffers of the "Good" series [including N-2-hydroxyethylpiperazine-$N^1$-2-ethanesulfonic acid (HEPES), 3-(N-morpholino)propanesulfonic acid (MOPES), and N-tris(hydroxymethyl)methyl-2-amenoethanesulfonic acid (TES)], tris(hydroxymethyl)aminomethane (TRIS), glycine buffers, buffers of salts of acetic and malic acids, and ammonium salt buffers. In keeping with the proposed mode of activity of reagents of the invention as effective in enhancing mitochondrial activity, such buffering agents as are compatible with in vitro activity of mitochondrial suspensions [see, e.g., Stinson et al., *Canadian Journal of Biochemistry*, Vol. 46, pp. 43-50 (1968)] are expected to be effectively employed in practice of the invention.

Benefits of the invention can be obtained through practice of a variety of treatment processes. It is possible, for example, to treat both seeds and seedlings with dry or aqueous AMP and buffering agent, or mixtures thereof, to produce growth characteristic enhancement. The clearly preferred methods include the use of aqueous solutions of mixtures of one or more nucleoside and/or nucleotide and the buffering agent, inasmuch as such methods allow uniform, simultaneous application of operative components. Aqueous solutions may be employed in seed treatment as a soak or spray for the seeds or may be applied to the seed bed. In treatment of seedlings, aqueous solutions may be used as a spray or soak for the seedlings during a transplanting procedure. Aqueous solutions of treating materials, when properly handled, are generally stable for extended periods of storage and have the advantage of easily fitting into existing schemes for the commercial processing of seed. In this respect, the solutions may serve as liquid carriers for the application of other soluble treatment materials and as wetting substances facilitating application of insoluble powdered treating agents such as fungicides.

It has been found that very small quantities of nucleoside or nucleotide can be employed to achieve substantial enhancement of growth characteristics. Buffered solutions of AMP at concentrations $1 \times 10^{-6}$ M or lower can provide growth enhancement when used as seed treating soaks or sprays. Preferred AMP concentrations in such solutions are on the order of $2 \times 10^{-2}$ M.

It has also been found that aqueous nucleotide or nucleoside solutions with very low concentrations of buffering agent can be employed without substantial loss of effectiveness. AMP solutions containing as little as $1 \times 10^{-3}$ M concentration of a sodium phosphate buffering agent can be employed as seed treating materials. Preferred buffering agent concentrations in such solutions are on the order of $1 \times 10^{-1}$.

The pH of buffered solutions can vary within a rather wide range without loss of effectiveness. AMP solutions buffered with sodium phosphate ranging from about pH 3.0 to about 12.0 can be employed with good results. The preferred solution pH for treating materials is at or around pH 7.0.

Practical considerations directing selection of a particular pH and buffer concentration for treatment solutions according to the invention can include such factors as the condition of the seeds at time of treatment. Acid delinted cotton seed could be predicted to be less effectively treated if the pH of a buffered AMP solution were very high and the concentration of buffering agent were very low. Under such circumstances, the effectiveness of the buffering agent could be rapidly diminished through "neutralization" and consequent salt formation by residual acid on the seed surface.

In keeping with the proposed mode of activity of nucleosides and nucleotides as effective in enhancing plant cell mitochondrial efficiency, the degree of enhancement of growth characteristics attending practice of the invention can be expected to vary, depending upon the particular plant treated and the degree to which the plant is subjected to environmental stresses. It has been found that the most substantial benefits generally attend treatment of seed crops which are cold sensitive and must be planted before uniform warm weather conditions can be assured. Cotton, sugar beet, jojoba, alfalfa and other cold sensitive crops all benefit from the invention. While maize is expected to be beneficially treated according to the invention, inbred lines of maize used in the hybridization process are expected to benefit more from treatment than hybird maize (due to the existing enhanced mitochondrial efficiency of the hybrid).

In a like manner, seed crops characterized by poor germination and seedling vigor in highly alkaline and saline soils and/or poor resistence to pathogens such as fungi can be expected to benefit substantially from treatment. As noted in detail infra, treatment of cracked and otherwise damaged seed according to the invention will substantially enhance growth characteristics.

Enhancement of growth characteristics obtained by practice of the invention may be easily quantified. Most noticeable are increases in the germination percentage of stocks of seeds treated with compositions according to the invention. Quite frequently, the rapidity of germination will be increased and measurements of other standard indications of seedling vigor—radicle weight, fresh and dry total plant weight, and the like—will be increased. Such effects on seedling emergence and vigor extend over the initial periods of seedling growth and long-term effects on total crop are easily projected and verified.

The following examples illustrate various aspects of practice of the invention.

EXAMPLE 1

A study was conducted to determine the effects of treatment of acid delinted, non-fungicide treated Pima S-4 cotton seed with buffered solutions containing varying concentrations of AMP. One hundred ml. of approximately $1 \times 10^{-1}$ M phosphate buffer solution was prepared by mixing, with stirring, 1.42 grams of $Na_2HPO_4$ and 0.28 g. $NaH_2PO_4$ in approximately 100 ml. of distilled water. The mixture pH was adjusted to 7.0 and brought up to volume. Aliquots of the buffer solution were used to prepare treating solutions having AMP concentrations varying from $2 \times 10^{-2}$ to $2 \times 10^{-6}$ M. One ml. of each treating solution and a water control were each used to treat about 60 grams of seed by means of vigorous shaking for 30 seconds in a covered beaker. Seed was spread out and rapidly air-dried following treatment, then held in standard paper coin envelopes until planting or germination testing. Seed was germinated as aseptically as possible on blotters in covered plastic trays in the dark. Seed was kept at 15° C. for 48 hours and then 22° C. for 72 hours, at which time germination percentages were calculated on the basis of means of four replications for each treatment with approximately 75 seeds per tray. Radicles were excised from twenty vigorous seedlings from each of the four replicate trays for each treatment. The results of the study are set out in Table 1 below. The germination percentages and radicle weights, in grams, are reported as means, ± standard error.

TABLE I

| AMP CONCENTRATION | GERMINATION % | RADICLE WEIGHT |
|---|---|---|
| ($H_2O$ Control) | 76 ± 0.3 | 0.8 ± 0.07 |
| $2 \times 10^{-2}$ M | 81 ± 2.6 | 1.2 ± 0.03 |
| $2 \times 10^{-3}$ M | 78 ± 2.3 | 1.0 ± 0.07 |
| $2 \times 10^{-4}$ M | 81 ± 3.1 | 1.0 ± 0.07 |
| $2 \times 10^{-5}$ M | 78 ± 3.3 | 1.1 ± 0.07 |
| $2 \times 10^{-6}$ M | 78 ± 1.0 | 1.0 ± 0.09 |

Each of the treatment solutions provided better results than the water controls, with the best results in both germination percentages and radicle weight being obtained at the $2 \times 10^{-2}$ M AMP concentrations.

EXAMPLE 2

A study was conducted to determine the effects of treatment of acid delinted, non-fungicide treated Pima S-4 cotton seed with $2 \times 10^{-2}$ M AMP solutions containing varying concentrations of sodium phosphate buffer. One hundred ml. of 1.0 M $Na_2HPO_4/NaH_2PO_4$, pH 7.0 buffer was prepared in the manner of the previous example. Several tenfold dilutions were made to adjust buffer concentrations to between 1.0 M and $1 \times 10^{-3}$ M and AMP was added to complete the treating solutions. The experimental protocol thereafter duplicated that of Example 1. Mean germination percentages and mean radicle weights in grams are set out in Table 2.

TABLE 2

| BUFFER CONCENTRATION | GERMINATION % | RADICLE WEIGHT |
|---|---|---|
| ($H_2O$ Control) | 76 ± 0.3 | 0.8 ± 0.07 |
| 1.0 M | 77 ± 3.1 | 0.9 ± 0.05 |
| $1 \times 10^{-1}$ M | 81 ± 2.6 | 1.2 ± 0.03 |
| $1 \times 10^{-2}$ M | 78 ± 0.5 | 1.1 ± 0.07 |
| $1 \times 10^{-3}$ M | 81 ± 2.1 | 1.0 ± 0.09 |

Each of the treatment solutions provided better results than the water controls, with the best results in both germination percentages and radicle weight being obtained at the $1 \times 10^{-1}$ M buffer concentration.

EXAMPLE 3

A study was conducted to determine the effects of treatment of acid delinted, non-fungicide treated Pima S-4 cotton seed with $2 \times 10^{-2}$ M AMP solutions in $1 \times 10^{-1}$ M sodium phosphate buffer at varying pH levels. One hundred ml. of $1 \times 10^{-1}$ M $Na_2HPO_4/NaH_2PO_4$ buffer solution was prepared in the manner of Example 1. Equal volume aliquots of the solution were adjusted with acid or base to pH's varying from 3.2 to 12.0. Suitable quantities of AMP were added to generate the treating solutions. The lowest pH buffer solution was heated to permit more rapid dissolving of the AMP. The experimental protocol thereafter duplicated that of Example 1. Mean germination percentages and mean radicle weights in grams are set out in Table 3.

TABLE 3

| SOLUTION pH | GERMINATION % | RADICLE WEIGHT |
|---|---|---|
| $H_2O$ control | 76 ± 2.9 | 1.2 ± 0.12* |
| pH 3.2 | 83 ± 2.1 | 1.2 ± 0.05 |
| pH 6.0 | 81 ± 1.4 | 1.3 ± 0.08 |
| pH 7.0 | 80 ± 0.7 | 1.3 ± 0.05 |
| pH 8.0 | 74 ± 5.6 | 1.1 ± 0.12 |
| pH 12.0 | 77 ± 4.3 | 1.4 ± 0.18 |

*Data considered unreliable and biased due to fungus growth in control trays. Cf. control values in Tables 1 and 2.

Each of the treatments provided better results in either germination percentage or radicle weight than the controls (if corrected for upward bias of radicle weight due to fungus growth). The best overall results were achieved at pH 3.2, 6.0 and 7.0 but, as noted above, because heating was needed to assist solution of AMP at pH 3.2, treating solutions having a pH of about 7.0 are preferred.

EXAMPLE 4

Table 4 below illustrates variations in percentage of germination of Pima S-4 cotton seed after pre-treatment with solutions of $2 \times 10^{-2}$ M AMP in 5 different 0.12 M buffers having an adjusted pH of 7.0. The treated seed and water treated controls were maintained in trays as in Example 1 at 15° for 72 hours and then at room temperature for 48 hours, after which the measurements were taken. The percentage germination was measured using four replicate trays per treatment and control in each of three experimental runs. The data are reported in means, ± standard error.

TABLE 4

| BUFFER | EXPT. 1 | EXPT. 2 | EXPT. 3 | MEAN |
|---|---|---|---|---|
| None ($H_2O$ Control) | 72 ± 2.8 | 70 ± 1.6 | 66 ± 2.7 | 69 |
| HEPES | 79 ± 1.3 | 74 ± 3.6 | 71 ± 5.2 | 75 |
| TRIS | 68 ± 1.0 | — | 63 ± 2.9 | 66 |
| Sodium Phosphate | 74 ± 2.5 | 71 ± 1.7 | 74 ± 1.8 | 73 |
| Potassium Phosphate | 73 ± 6.4 | 72 ± 2.3 | 71 ± 3.2 | 72 |

TABLE 4-continued

| BUFFER | EXPT. 1 | EXPT. 2 | EXPT. 3 | MEAN |
|---|---|---|---|---|
| Ammonium Phosphate | 80 ± 3.1 | 75 ± 1.9 | 70 ± 3.0 | 75 |

Table 5 below illustrates variations in the fresh weights of roots under treatment conditions employed to generate the percentage germination data in Table 4. The data given are the means of four replicated measurements of fresh weight of 20 roots each, in grams, ± the standard error. With the exception of TRIS, each of the buffers selected numerically increases germination percentages.

TABLE 5

| BUFFER | EXPT. 1 | EXPT. 2 | EXPT. 3 | Mean |
|---|---|---|---|---|
| None (H$_2$O Control) | 0.78 ± 0.03 | 0.83 ± 0.06 | 0.96 ± 0.03 | 0.86 |
| Hepes | 1.19 ± 0.10 | 0.98 ± 0.09 | 0.80 ± 0.03 | 0.99 |
| Tris | 0.98 ± 0.05 | — | 0.96 ± 0.08 | 0.97 |
| Sodium Phosphate | 0.99 ± 0.03 | 0.95 ± 0.03 | 1.04 ± 0.04 | 0.99 |
| Potassium Phosphate | 1.10 ± 0.04 | 0.90 ± 0.06 | 0.96 ± 0.03 | 0.99 |
| Ammonium Phosphate | 1.13 ± 0.03 | 0.98 ± 0.05 | 0.88 ± 0.06 | 1.00 |

Each of the treatment solutions provided better results in either germination percentage or fresh root weight than the water control.

EXAMPLE 5

Field studies were conducted in an attempt to quantify comparative results of treatment according to the invention and other treatments. Equal quantities of acid delinted Pima S-4 cotton seed received the following pretreatments before planting: (1) soaking in water; (2) soaking in an aqueous, pH 7.0 solution of $2 \times 10^{-2}$ M AMP buffered with $1 \times 10^{-1}$ M sodium phosphate; (3) soaking in an aqueous solution of $2 \times 10^{-1}$ M AMP; (4) soaking in a dichloromethane solution of $2 \times 10^{-2}$ M AMP; and (5) no pretreatment (untreated control). Seed was planted in Marana and Safford Airzona. For each treatment, eight randomized field plots of seedlings were characterized in terms of potential stand (number of seedlings per 100 seed planted) and time interval to 50% emergence. Mean field stand results, ± standard error, are set out in Table 6 and mean 50% emergence results, in days ± standard error, are set out in Table 7.

TABLE 6

| TREATMENT | MARANA, AZ. | SAFFORD, AZ. |
|---|---|---|
| Untreated Control | 65.7 ± 1.9 | 56.7 ± 2.1 |
| Water Control | 66.5 ± 3.0 | 54.7 ± 1.7 |
| AMP/ Buffer | 69.0 ± 2.0 | 55.9 ± 2.0 |
| AMP only | 64.6 ± 0.7 | 53.2 ± 2.4 |
| AMP + dichloromethane | 64.0 ± 1.4 | 50.5 ± 1.5 |

TABLE 7

| TREATMENT | MARANA, AZ. | SAFFORD, AZ. |
|---|---|---|
| Untreated Control | 10.05 ± 0.05 | 11.16 ± 0.38 |
| Water Control | 10.09 ± 0.10 | 11.31 ± 0.27 |
| AMP/Buffer | 10.06 ± 0.09 | 11.16 ± 0.24 |
| AMP only | 9.81 ± 0.07 | 11.22 ± 0.26 |
| AMP + dichloromethane | 10.01 ± 0.11 | 11.40 ± 0.28 |

Table 8 reports the results of potential stand and 50% emergence field studies conducted in Phoenix, Arizona test fields. Treatments and controls were the same as in the tests reported in Tables 6 and 7, except that the AMP/dichloromethane treatment was replaced in the experimental scheme by soaking in an aqueous solution of the $1 \times 10^{-1}$ M phosphate buffer (pH 7.0) alone.

TABLE 8

| ENTRY | POTENTIAL STAND | DAYS TO 50% EMERGENCE |
|---|---|---|
| Untreated Control | 65.7 ± 2.8 | 13.04 ± 0.13 |
| Untreated Control | 61.0 ± 4.0 | 12.81 ± 0.24 |
| Water Control | 66.7 ± 3.4 | 13.19 ± 0.18 |
| Water Control | 67.4 ± 2.3 | 13.06 ± 0.13 |
| AMP/Buffer | 67.0 ± 2.9 | 12.99 ± 0.34 |
| AMP/Buffer | 65.9 ± 3.1 | 12.96 ± 0.26 |
| AMP/Buffer | 66.9 ± 2.5 | 13.15 ± 0.25 |
| AMP/Buffer | 62.9 ± 3.0 | 13.02 ± 0.32 |
| AMP only | 63.2 ± 2.1 | 13.07 ± 0.22 |
| AMP only | 61.2 ± 3.9 | 12.81 ± 0.26 |
| Phosphate buffer only | 62.1 ± 2.9 | 12.56 ± 0.12 |
| Phosphate buffer only | 61.0 ± 1.9 | 13.01 ± 0.16 |

EXAMPLE 6

Tables 9 through 12 report the results of field studies in different locations comparing growth characteristics of untreated (control) seed and seed pretreated with an aqueous solution of $2 \times 10^{-2}$ M AMP in a pH 7.0 buffer of $1 \times 10^{-1}$ M phosphate. Pima S-5 L seed was used in each study. Table 9 provides data on the mean fresh weights, in grams, ± standard error, of 10 whole plants drawn randomly from four fields at the first location by several investigators.

TABLE 9

| REPLICATION | CONTROL | AMP/ BUFFER TREATED | TREATMENT AS % OF CONTROL |
|---|---|---|---|
| 1. | 42.6 | 54.0 | 127 |
| 2. | 45.4 | 76.7 | 169 |
| 3. | 56.8 | 56.8 | 100 |
| 4. | 39.8 | 45.4 | 114 |
| Field Mean | 46.1 ± 3.7 | 58.2 ± 6.5 | 127 |

Table 10 provides data on the mean fresh weights in grams, ± standard error, for whole plants randomly selected from fields at the second location. Eight replications of the selection were carried out.

TABLE 10

| REPLICATION | CONTROL | AMP/ BUFFER TREATED | TREATMENT AS % OF CONTROL |
|---|---|---|---|
| 1 | 68.2 | 73.8 | 108 |
| 2 | 102.2 | 113.6 | 111 |
| 3 | 82.4 | 85.2 | 103 |
| 4 | 96.6 | 102.2 | 106 |
| 5 | 99.4 | 102.2 | 103 |
| 6 | 113.6 | 125.0 | 110 |
| 7 | 82.4 | 119.3 | 144 |
| 8 | 93.7 | 113.6 | 121 |
| Field Mean | 92.3 ± 5.0 | 104.4 ± 6.2 | 113 |

Table 11 provides data on mean seedling dry weights in grams ± standard error, for 10 whole plants randomly selected from fields at the second location. Eight replications of the selection were carried out.

TABLE 11

| REPLICATION | CONTROL | AMP/BUFFER TREATED | TREATMENT AS % OF CONTROL |
| --- | --- | --- | --- |
| 1 | 14.3 | 15.2 | 106 |
| 2 | 16.6 | 17.1 | 103 |
| 3 | 19.6 | 19.9 | 101 |
| 4 | 16.8 | 25.2 | 150 |
| 5 | 19.9 | 21.9 | 110 |
| 6 | 19.1 | 21.7 | 114 |
| 7 | 22.8 | 24.7 | 108 |
| 8 | 19.2 | 22.4 | 117 |
| Field Mean | 18.5 ± 0.92 | 21.0 ± 1.23 | 114 |

Table 12 provides data on mean seedling dry weights, in grams ± standard error, for 12 randomly selected pairs of treated and control plants at the third location.

TABLE 12

| SAMPLE | CONTROL | AMP BUFFER TREATED | TREATMENT AS % OF CONTROL |
| --- | --- | --- | --- |
| 1 | 9.19 | 6.94 | 76 |
| 2 | 5.12 | 12.19 | 238 |
| 3 | 10.30 | 9.35 | 91 |
| 4 | 4.38 | 7.02 | 160 |
| 5 | 7.72 | 13.00 | 168 |
| 6 | 6.88 | 8.90 | 129 |
| 7 | 6.69 | 8.86 | 132 |
| 8 | 5.19 | 7.50 | 144 |
| 9 | 8.43 | 6.22 | 73 |
| 10 | 5.28 | 7.24 | 137 |
| 11 | 6.12 | 8.53 | 139 |
| 12 | 2.14 | 6.44 | 300 |
| Mean | 6.45 ± 0.65 | 8.51 ± 0.62 | 148.9 |

EXAMPLE 7

Field studies were conducted at two locations (Marana and Safford, Arizona) to illustrate the effectiveness of treatment of acid delinted cotton seed in enhancing emergence characteristics of poor quality, cracked seed. Treated seed was soaked in an aqueous solution of $2 \times 10^{-2}$ M AMP buffered at pH 7.0 with $1 \times 10^{-1}$ M phosphate. Control seed as water soaked. Table 13 reports mean germination percentages, ± standard error, for eight randomized field plots. Table 14 reports days to 50% germination for the same plots.

TABLE 13

| LOCATION | CONTROL | AMP/BUFFER TREATED | TREATMENT AS % OF CONTROL |
| --- | --- | --- | --- |
| Marana | 31.9 ± 1.0 | 38.4 ± 2.0 | 120 |
| Safford | 27.0 ± 2.0 | 31.4 ± 2.0 | 115 |

TABLE 14

| LOCATION | CONTROL | AMP/BUFFER Treated | TREATMENT AS % of control |
| --- | --- | --- | --- |
| Marana | 10.72 ± 0.20 | 10.66 ± 0.19 | 99 |
| Safford | 12.51 ± 0.42 | 12.46 ± 0.22 | 100 |

EXAMPLE 8

Studies were conducted determining the effects on resistance to fungus by seed treatment according to the invention. In a first study, acid delinted P-28 cotton seed was treated with an aqueous solution of $2 \times 10^{-3}$ M AMP buffered at pH 7.0 with $1 \times 10^{-1}$ M phosphate. Controls were water treated. A one-third portion of the seed was dusted with Captan ® fungicide prior to AMP/buffer or water treatment and another one-third portion was dusted with the fungicide after AMP/buffer or water treatment. The remaining seed was not treated with fungicide. All seed was germinated in uncovered plastic trays on brown paper towels at 16° for 2 days and 22° C. for 2½ days, at which time germination percentages were calculated. The study involved two replications and the results are set out in Table 15.

TABLE 15

| TREATMENT | REPLICATION | NO FUNGICIDE | FUNGICIDE AFTER TREATMENT | FUNGICIDE BEFORE TREATMENT |
| --- | --- | --- | --- | --- |
| Water Control | 1 | 81.9 | 80.3 | 79.3 |
|  | 2 | 80.6 | 84.3 | 79.3 |
| AMP/Buffer Treatment | 1 | 89.5 | 80.8 | 75.0 |
|  | 2 | 96.3 | 77.2 | 80.5 |

Briefly summarized, the data indicate that buffered AMP treatment alone had salutary effects on enhencing resistance to fungus infection and that varying the sequence of serial buffered AMP and fungicide treatments had no substantial effects on germination percentages. The general effects of the fungicide treatment were unexpectedly low. While not experimentally confirmed, the observed lessening of effectiveness of the fungicide may be attributed to the use of multiple aqueous treatments. Consistent with present practices in seed treatment, it is believed that treatment of seed according to the invention will be most effective in enhancing resistance to environmental stresses when carried out as an element of a composite single treatment with other desired treating agents.

A second study relating to resistance to fungus of seed treated according to the invention provided remarkable evidence of fungistatic effects of treatment with respect to at least one cotton pathogen, *Thielaviopsis basicola*—a low temperature fungus prevelant as a "damping off" disease in most cotton production areas of the United States. Approximately one thousand pounds of Pima S-5 cotton seed was treated during commercial acid delinting processing with about five gallons of an aqueous solution of $2 \times 10^{-2}$ M AMP buffered at pH 7.0 with $1 \times 10^{-1}$ M phosphate. The buffered AMP was co-applied with a standard dosage of "Captan/PCMB" fungicide as a liquid slurry. An equal amount of control seed was identically processed, except that the fungicide slurry contained five gallons of water. The treated and control seed was planted in adjacent rows on a commercial field in Marana, Arizona. After about three and one-half weeks, many seedlings exhibited signs of fungal infection. A total of about eight hundred seedlings (equally divided between treated and control groups) were selected randomly from within eight field areas and examined for obvious evidence of a diseased state. Table 16 reports the mean number of obviously diseased plants per sample of 10 seedlings in given field areas. The pathogen was later confirmed as *Thielaviopsis basicola*.

TABLE 16

| FIELD AREA | DISEASED PLANTS CONTROL | DISEASED PLANTS AMP/BUFFER |
|---|---|---|
| SW 1 | 9 | 0 |
| SW 2 | 10 | 1 |
| SE 1 | 10 | 1 |
| SE 2 | 6 | 0 |
| NW 1 | 10 | 2 |
| NW 1 | 7 | 0 |
| NE 1 | 10 | 0 |
| NE 2 | 6 | 1 |
| Mean % Diseased | 85 % | 6% |

EXAMPLE 9

A field study was conducted to determine the effect on lint yield brought about by treatment of Pima S-5 acid delinted cotton seed. Seed was treated with an aqueous solution of $2 \times 10^{-2}$ M AMP buffered at pH 7.0 with $1 \times 10^{-1}$ phosphate buffer. Controls were untreated. Treatment was made during commercial delinting processing which included application of fungicide. Seed was planted at a rate of 13 pounds per acre in four multi-acre plots in Marina, Arizona. Table 17 reports lint yields both in terms of pounds per acre on the first pick and the final yield.

TABLE 17

| TREATMENT | PLANT POPULATION (PER ACRE) | FIRST PICK | FINAL YIELD |
|---|---|---|---|
| Control | 31,500 | 769 | 805 |
| AMP/Buffer | 39,000 | 796 | 828 |
| Treatment as % of Control | 123 | 104 | 103 |

The increases in lint yield of the treated seed can be translated to approximately $20.00 additional profit per acre.

The data reported in Tables 7 through 9 generally illustrate the enhanced effectiveness of the use of buffering agents in combination with nucleoside or nucleotide treatment of seed. Further illustration of the advantages obtained through practice of the invention is supplied by gross analysis of relative increases in various growth parameters obtained in the course of the inventors' early work with AMP solutions as compared to later work involving treatment with AMP solutions and buffering agents. Table 18 provides data concerning 24 field studies directed to determining the effects of AMP treatments on seed of a number of cotton varieties with enhancement reported in terms of overall effect of treatment as a percentage of controls. Table 19 reports data from 21 field studies involving cotton seed treatment with both AMP and a buffering agent. In each Table the average effect attributable to treatment is reported. The analysis reveals substantially greater enhancement in the measured growth parameters resulting from AMP and buffering agent treatment than achieved by AMP treatment alone.

TABLE 18

| TEST NO. | COTTON VARIETY | TREATMENT AS % OF CONTROL | PARAMETER MEASURED |
|---|---|---|---|
| 1 | S-4 | 110 | fresh wt. |
| 2 | S-4 | 99 | fresh wt. |
| 3 | S-4 | 117 | germination % |
| 4 | S-4 | 106 | germination % |
| 5 | DPL-16 | 127 | germination % |
| 6 | DPL-16 | 119 | germination % |
| 7 | S-4 | 108 | germination % |
| 8 | P-28 | 111 | germination % |
| 9 | P-29 | 90 | germination % |
| 10 | S-4 | 87 | germination % |
| 11 | ST-213 | 96 | germination % |
| 12 | DPL-16 | 92 | germination % |
| 13 | DPL-66 | 93 | germination % |
| 14 | ST-256 | 93 | germination % |
| 15 | DPL-16 | 100 | germination % |
| 16 | DPL-16 | 92 | germination % |
| 17 | DPL-61 | 97 | germination % |
| 18 | DPL-66 | 114 | germination % |
| 19 | ST-213 | 103 | germination % |
| 20 | ST-256 | 120 | germination % |
| 21 | P-28 | 108 | germination % |
| 22 | S-5 | 98 | germination % |
| 23 | P-28 | 94 | germination % |
| 24 | P-29 | 105 | germination % |

Average % advantage attributable to treatment = $103.3 \pm 2.2$

TABLE 19

| TEST NO. | COTTON VARIETY | TREATMENT AS % OF CONTROL | PARAMETER MEASURED |
|---|---|---|---|
| 1 | S-5 | 109 | germination % |
| 2 | S-5 | 124 | germination % |
| 3 | S-5 | 94 | germination % |
| 4 | S-5 | 111 | germination % |
| 5 | S-5 | 101 | fresh wt. |
| 6 | S-5 | 112 | germination % |
| 7 | S-5 | 98 | germination % |
| 8 | S-5 | 113 | germination % |
| 9 | S-5 | 118 | fresh wt. |
| 10 | S-5 | 105 | germination % |
| 11 | S-5 | 147 | germination % |
| 12 | S-5 | 100 | germination % |
| 13 | S-5 | 104 | germination % |
| 14 | S-5 | 99 | germination % |
| 15 | S-5 | 120 | germination % |
| 16 | S-5 | 97 | germination % |
| 17 | S-5 | 116 | germination % |
| 18 | S-5 | 126 | fresh wt. |
| 19 | S-5 | 113 | fresh wt. |
| 20 | S-5 | 114 | dry wt. |
| 21 | S-5 | 132 | dry wt. |

Average % advantage attributable to treatment = $112.1 \pm 2.8$

Compositions of the invention include dry and aqueous mixtures of one or more nucleosides and/or nucleotides and the selected buffering agent. As an example, a dry mixture of 0.74 grams of AMP with 1.42 grams of $Na_2HPH_4$ and 0.28 grams of $NaH_2PO_4$ is expected to be storage stable for long periods of time and can be made up to an appropriate treating solution upon the addition of 100 ml. of water. The concentration of AMP will be about $2 \times 10^{-2}$ M and the buffer concentration will be about $1 \times 10^{-1}$. The pH will be approximately 7.0. Seed treated with the appropriate solution may be stored in commercial, 50 pound bilayer paper bags for the customary period preceding planting without adverse effects.

Also contemplated by the invention are solutions, suspension and emulsions of a mixture of one or more nucleosides and/or nucleotides and buffering agent in non-aqueous liquids, including those which may be employed in effecting other desired seed treatments, e.g., with fungicides and insecticides. Suitability of any particular non-aqueous liquid as a vehicle for treatment of seeds and seedlings according to the invention may be easily determined without undue experimentation. As indicated in Example 5 above, for example, AMP treatment is compatible with use of dichloromethane which, in turn, is likely to be equally compatible with many buffering agents. Routine preliminary screening to date has revealed that AMP and buffering agent treatment may effectively proceed through use of a non-ionic detergent liquid vehicle such as Triton X-100 (Rohm & Haas), but that dimethylsulfoxide is an ineffective vehicle. Dry reagent mixtures of the invention may also be employed as a portion of a dry mix of "clay pellet" seed coating, or with coating materials such as diatomaceous earth.

Obviously, numerous modifications and variations of the above-illustrated inventions are expected to occur to those skilled in the art and therefore only such limitations as appear in the appended claims should be placed thereon.

What is claimed is:

1. In the process for enhancement of growth characteristics of plant seed and seedlings which consists of treating with an effective amount of one or more nucleosides and/or nucleotides, the improvement comprising treating with an effective amount of a non-phytotoxic buffering agent to provide a quantitative ratio of $1 \times 10^{-6}$ to $2 \times 10^{-2}$ moles of nucleoside and/or nucleotide per 1 to $1 \times 10^{-3}$ moles of buffering agent.

2. The improvement of claim 1 wherein said nucleosides and/or nucleotides are administered concurrently with said buffering agent in the form of an aqueous solution.

3. The improvement of claim 2 consisting of concurrently administering adenosine monophosphate and a buffering agent consisting of a mixture of phosphoric acid salts in an aqueous solution having a pH of from about 3.0 to about 12.0.

4. The improvement of claim 3 wherein the material to which said aqueous solution is administered is a plant seed.

5. The improvement of claim 4 wherein said plant seed is cotton seed.

6. A composition of matter for use in the treatment of plant seed and seedlings to enhance growth characteristics thereof, said composition comprising a dry mixture of one or more nucleosides or nucleotides and a non-phytotoxic buffering agent in a quantitative ratio providing from $1 \times 10^{-6}$ to $2 \times 10^{-2}$ moles of nucleoside or nucleotide per 1 to $1 \times 10^{-3}$ moles of buffering agent.

7. A composition according to claim 6 in combination with an aqueous solvent.

8. A composition according to claim 6 comprising adenosine monophosphate and salts of phosphoric acid.

9. A method of enhancing the resistance of plant seed to environmental stress during germination, said method comprising treating the seed with an aqueous solution of from $1 \times 10^{-6}$ to $2 \times 10^{-2}$ M adenosine monophosphate buffered at about pH 7.0 with a non-phytotoxic buffering agent at a solution concentration of from about 1 to about $1 \times 10^{-3}$ M.

10. The method of claim 9 wherein said buffering agent comprises salts of phosphoric acid.

* * * * *